US007790178B2

(12) United States Patent
Gore et al.

(10) Patent No.: US 7,790,178 B2
(45) Date of Patent: Sep. 7, 2010

(54) TRIVALENT VACCINE WITH MATERNAL ANITBODY TRANSFER VIA THE MILK

(75) Inventors: Thomas Gore, Salisbury, MD (US); Adrian Mockett, Warboys Hungtington (GB)

(73) Assignee: Intervet International B.V., Boxmeer (NL)

( * ) Notice: Subject to any disclaimer, the term of this patent is extended or adjusted under 35 U.S.C. 154(b) by 78 days.

(21) Appl. No.: 10/539,670

(22) PCT Filed: Dec. 18, 2003

(86) PCT No.: PCT/US03/40823

§ 371 (c)(1),
(2), (4) Date: Jan. 5, 2006

(87) PCT Pub. No.: WO2004/056390

PCT Pub. Date: Jul. 8, 2004

(65) Prior Publication Data

US 2006/0140976 A1 Jun. 29, 2006

Related U.S. Application Data

(60) Provisional application No. 60/434,683, filed on Dec. 19, 2002.

(51) Int. Cl.
*A61K 39/295* (2006.01)
(52) U.S. Cl. .................................... 424/202.1
(58) Field of Classification Search ........................ None
See application file for complete search history.

(56) References Cited

U.S. PATENT DOCUMENTS

| | | | | | |
|---|---|---|---|---|---|
| 4,193,990 | A | * | 3/1980 | Appel et al. | 424/233.1 |
| 4,193,991 | A | * | 3/1980 | Appel et al. | 424/233.1 |
| 4,971,793 | A | * | 11/1990 | Wood et al. | 424/233.1 |
| 5,000,951 | A | * | 3/1991 | Bass et al. | 424/201.1 |
| 6,057,436 | A | * | 5/2000 | Miller et al. | 536/23.72 |
| 6,159,477 | A | * | 12/2000 | Audonnet et al. | 424/199.1 |
| 6,228,846 | B1 | * | 5/2001 | Audonnet et al. | 514/44 |
| 2001/0028884 | A1 | | 10/2001 | Poulet | |

FOREIGN PATENT DOCUMENTS

| EP | 0329264 | 8/1989 |
|---|---|---|
| WO | 9818453 | 5/1998 |
| WO | 0152887 | 7/2001 |

OTHER PUBLICATIONS

Waner et al. Assessment of Immunization Response to Canine Distemper Virus Vaccine in Puppies Using a Clinic-based Enzyme-linked Immunosorbant Assay, The Veterinary Journal, 1998, vol. 155, No. 2, p. 171-175>.*
Poulet et al. Protection of puppies against canine herpesvirus by vaccination of the dams, The Veterinary Record, Jun. 2001, vol. 148, No. 22, p. 691-695, abstract only.*
Mochizuki et al. Recent Epidemiological Status of Canine enteric Infections and Giardia Infections in Japan, Journal of Veterinary Medical Science, 2001, vol. 65, No. 5, p. 573-575.*
Schwartz et al. The Canine Minute Virus Is a Distinct Parvovirus That Is Most Similar to Bovine Parvovirus, Virology, Oct. 2002, vol. 32, No. 2, p. 219-223.*
Pratelli, et al., Immunization of Pups with Maternally Derived Antibodies to Canine Parvovirus Using a Modified-live Variant, Journal of Veterinary Medicine B, 2000, vol. 47, p. 273-276.*
Willem et al., Control of canine parvovirus infection in breeding kennels: Study of the efficacy of a high titer attenuated canine parvovirus vaccine, Revue de Medecine Veterinaire, 2001, vol. 152, No. 5, p. 373-378.*
Pratelli et al., Fatal canine parovvirus typr-1 infection in pups from Italy, Journal of Veterinary Diagnostic Investigation, 1999, vol. 11, pp. 365-367.*
Truyen, Recent Advances in Canine Infectious Diseases, International Veterinary Information Service, Jan. 2000, 6 pages.*
Poulet et al., Protection of puppies against canine herpesvirus by vacciniation of the dams. Veterinary Recoed, 2001, vol. 148, pp. 691-695.*
Julio Correa, Canine Breeding and Reproduction, Alabama Cooperative Extension System (ACES), Alabama A&M and Auburn Universities, Nov. 2002; UNP-52, 8 pages.*
Larson et al., Comparison of selected canine vaccines for their ability to induce protective immunity against canine parvovirus infection, American Journal of Veterinary Research, Apr. 1997, vol. 58, No. 4, pp. 360-363.*
Carmichael et al. Journal of Veterinary Diagnostic Investigation, 1994, vol. 6, pp. 165-174.*
McDonald, Veterinary Medicine, Mar. 1992, vol. 87, No. 3, pp. 223-230.*
Meloen et al. Biologicals, 2001, vol. 29, pp. 233-236.*
Virus Infections of Carnivores, Edited by Max J. Appel, 1987, pp. 12,63-67,1, Elsevier Science Publishers B.V.
Infectious Diseases of the Dog and Cat, Craig E. Greene, 1990, pp. 22-25 and 283-284, W.B. Saunders Co.
MaCartney, L. et al.: "Characterization of minute virus of canines (MVC) and its pathogenicity for pups" Cornell Veterinarian, 1988, 78:131-145.
Poulet, H. et al.: "Protection of puppies against canine herpesvirus by vaccination of the dams" The Veterinary Record, 2001, 148:691-695.
Engels, M. et al.: "Die Seroepizootologie der caninen Herpesvirusinfektion in der Schweiz und praliminare Versuche mit einer Vakzine" Zbl. Vet. Med. B., 1980, 27(4):257-267.
Valcic, M. "Humoral immunity in pregnant bitches and their puppies after Inoculation of six immunogens" ACTA Veterinaria, 1988, 38(4):171-180.
International Search Report for PCT/US2003/040823, published as WO 2004/056390, Jul. 8, 2004.
Infectious Diseases of the Dog and Cat, Craig E. Greene, 1990, pp. 279-281, W.B. Saunders Co.

* cited by examiner

*Primary Examiner*—Ali R. Salimi
(74) *Attorney, Agent, or Firm*—William M Blackstone; Aaron L. Schwartz

(57) ABSTRACT

Embodiments of the present invention generally relate to novel multivalent vaccines and methods of vaccinating. In an embodiment, the present invention is a trivalent vaccine for canine herpesvirus (CHV), canine rotavirus (CRV), and Minute virus of canine (MVC) or other canine parvovirus delivered to pups of a whelp through colostrums and providing sufficient antibody titer to impart protection.

11 Claims, No Drawings

TRIVALENT VACCINE WITH MATERNAL ANITBODY TRANSFER VIA THE MILK

CROSS REFERENCE TO RELATED APPLICATIONS

This application is a National Phase entry under 35 U.S.C. §371 of International Application No. PCT/US2003/040823, filed Dec. 18, 2003, which claims priority to U.S. Provisional Application No. 60/434,683, filed Dec. 19, 2002.

FIELD OF THE INVENTION

The present invention is related to a trivalent vaccine with an effective amount of maternal antibody transfer.

BACKGROUND OF THE INVENTION

Vaccination is a critical veterinary practice for the purpose of protecting healthy animals from infectious diseases. The intent of vaccination is to stimulate a protective humoral and/or cellular immune response in healthy animals to targeted disease organisms. Though vaccination usually begins between 6-9 weeks-of-age, the first vaccination can be administered as early as 3-weeks-of-age. However, at younger ages vaccine efficacy is dependent on the presence and concentration of maternal antibody.

For dogs it is generally accepted that in properly vaccinated bitches the passive transfer of maternal antibody through the placenta and by ingestion of colostrum will protect puppies from certain infectious diseases. Passively derived antibody received from the mother may circulate in the puppy for as long as 20 weeks. However, the duration of passive protection is dependent on the half-life of the antibody and amount of antibody transferred. In general the half-life of canine IgG antibody is 11-14-days. The concept of vaccinating pregnant bitches to passively protect newborn puppies from disease due to canine herpes has recently been implemented commercially.

However, it has not been demonstrated that a multivalent, inactivated vaccine could be administered to bitchs for the specific purpose of eliciting immunologically effective amounts of maternal antibodies for transfer to at least one pup after whelping. Consequently, puppy vaccines are currently given as early as four weeks of age and then repeated every three to four weeks, until sometime after twenty weeks of age. However, there are situations where, due to the level of circulating maternal antibodies, vaccination may fail to protect against a field challenge.

A newborn puppy is born with essentially no antibodies of its' own. Furthermore, its immune system requires several months to be fully competent. At birth, initial protection from pathogens that puppies comes into contact with is by the presence of circulating antibody passively derived from its' mother.

During the first 2 days after giving birth mother's milk contains high levels of her own antibodies. This antibody laden milk is known as colostrum. A newborn pup must ingest colostrum during the first 24 hrs after birth to obtain protective antibodies from its mother. After 24 hours the pup's gastrointestinal tract becomes more mature and the absorption of intact antibody protein molecules ceases. Antibody that is not absorbed is digestion and is no longer absorbed as functional molecules and transferred to the circulation. The amount of antibody absorbed depends on the quantity of colostrum ingested and the level of maternal antibody in the colostrum. Nursing pups will obtain an adequate amount of antibodies during the first 24 hours after birth if the circulating antibody level is high in the bitch. Conversely, if the antibody level (low antibody titer) in the bitch is low as a result of remote vaccination or poor immune response, then pups will receive an insufficient level of antibody for passive protection. Both of these situations have positive and negative results. If maternal antibody levels are low, or pups ingest a minimal amount of colostrums, the passively transferred antibody in the pups may be metabolized before the first vaccination is administered and a period of susceptibility to disease will exist. On the other hand, if the level of maternally derived antibody is high at the time of first vaccination, an active immune response in the pups will be minimal. High maternal antibodies levels will neutralize vaccine antigens preventing stimulation of the immune system. However, until an active immune response can be initiated in the puppy, the danger of a serious infection increases as the passive antibody level wane over time. The only way to evaluate the situation in an individual pup is to determine antibody titers before vaccination. Such a practice is expensive and not readily available. A basic rule of thumb is to assume that from about age 4 weeks until 15 weeks pups may not be adequately protected and until active immunity can be established care should be taken to limit environmental exposure.

The age at which a pup becomes susceptible to infection is determined primarily by the passive antibody titer at the time of exposure. Pups born to seronegative bitches are susceptible at birth; pups from bitches with low antibody titers may be susceptible as early as four to six weeks after birth, whereas pups from bitches with high titers may be immune to infection for 12 to 16 weeks.[4]

To increase the level of protection and/or the length of protection, pups can be immunized. However, common problem in vaccinating canines, such as dogs and puppies, is the maternal antibody interference during immunization. Maternal antibody interference is the most common cause of vaccine failure in weanling animals.[1] Maternal antibody neutralizes vaccine virus and suppresses a pup's active immune response. This common immunization problem occurs with all diseases, but is of particular concern in the case of the CPV's enteritis because of the explosive nature of disease transmission and because pups are at greatest risk of CPV-induced mortality.

Pups receive about 10% of their CPV maternal antibody via transplacental transfer and the remaining 90% through colostral absorption during the first 24 hours after birth.[3] At about three days of age, a pup's antibody titer usually equals that of its bitch. Because maternal antibody is not actively replaced, it declines at a predictable rate; a pup's titer falls by half about every 10 days or so.

Maternal CPV antibody would be much less problematic if pups remained protected from disease for as long as antibodies interfered with vaccination. However, there is a two-to five-week time period when antibody titers have declined so much that a pup is susceptible to virulent virus, but are still high enough to remain refractory to immunization with current vaccines.[1] Vaccinations given before or during this time period will not stimulate active immunity in the pup. [5]

Further potential problems with vaccines include choosing an appropriate vaccine regiment. Of concern in any vaccine regiment is the choice of vaccine. As a basic matter, the choices will include univalent and multi or polyvalent vaccines. Univalent vaccine will immunize an animal against one single disease. Polyvalent or multivalent vaccines can immunize against several diseases. There are killed vaccines, live vaccines, and attenuated vaccines (modified live). Different vaccines are made in different ways. Each has a good reason for use and also potential problems. Univalent vaccines require multiple injections of different vaccines to make sure coverage for several diseases is given. Multivalent vaccines can overwhelm an immune system and cause immune suppression making the pup susceptible to minor infections or illnesses that would otherwise not affect him. Killed vaccines are not as effective in stimulating the immune system to make antibodies while modified-live (ML) vaccines reproduce in the animal's body and result in a higher antibody response. ML vaccines can also cause illness in the animal because they do reproduce and viruses are shed in feces or urine or saliva and bacteria are also shed until the animal is able to fight off the infection and kill the remaining organisms. Also ML vaccines can revert to the infective (virulent) form or even to a more virulent form and can contaminate the environment with viruses and bacteria that are infective to wild animals, birds, or even people. Vaccines which are made in chicken eggs can also stimulate the dog to be very allergic to eggs or chickens. Vaccines made in feline cell cultures can be fine the first time used and create a severe reaction the second shot because the dog may have made antibodies to the feline cells. Proteins from even the canine cell cultures can stimulate the pup to make antibodies that will attack it's own thyroid, adrenal, blood cells, nerve cells or essentially any of his own body tissues and result in mild to life threatening autoimmune diseases. The ML vaccines can contain undetected viruses gotten from the cell culture material that can also cause serious problems. ["A Brief Review of Canine Neonatal Immunology" found on the website of Versatility in Poodles, Inc. at http://web.foothill.net/vipoodle/neoim.htm.]

However, even with all these problems and/or difficulties, vaccination is recommended. The choice of vaccine regiments should be coordinated through a veterinarian and made on the basis of the specie of canine and/or other animal. ["A Brief Review of Canine Neonatal Immunology" found on the website of Versatility in Poodles, Inc. at http://web.foothill.net/vipoodle/neoim.htm.]

There is currently no all-killed multivalent vaccine on the market. Attempts have been made, but without success. The prior art discloses that multivalent vaccines are very difficult to manufacture an all-killed multivalent vaccine that will stimulate the immune system to make antibody against all the components equally. [See "A Brief Review of Canine Neonatal Immunology" found on the website of Versatility in Poodles, Inc. at http://web.foothill.net/vipoodle/neoim.htm.]

Some veterinary experts are recommending that after the first puppy immunizations the dog be tested for antibody level (titers) to see if they actually need a booster. Some dogs never need another booster, others need several boosters.

Accordingly, the art field is in search of an effective vaccine that protects pups without the attendant interference experienced from maternal antibodies, as explained above.

Of particular concern to young puppies are the diseases of Canine Rota Virus (CRV), Canine Herpesvirus (CHV), Minute Virus of Canines (MVC). Typically, a pups immnune system will grow and develop protection to these diseases within the first few months of life. Unfortunately, transmission of the disease to young pups can have detrimental effects on their condition and/or development. To further complicate, the problems associated with varying maternal antibody transfer to pups at whelp and effectiveness of that transfer make it difficult to assure vaccination of all pups in the whelp, even assuming that all pups consume an appropriate amount of colostrums.

Two distinct parvoviruses (CPV), are now known to infect dogs—the pathogenic CPV-2, which was recognized as a new disease of dogs and wild canines in 1978, and the "minute virus of canines" (MVC, CPV-1) reported by Binn in 1970. MVC, a completely different parvovinis, had not been associated with natural disease until 1992. MVC may cause pneumonia, myocarditis and enteritis in young pups, or transplacental infections in pregnant dams, with embryo resorptions and fetal death.

Information about Canine parvovirus (CPV and CPV-1) is available through most mediums. For instance, the website http://www.hagen.com/uk states that CPV is an acute, highly contagious, gastro enteritis of primarily young dogs (peak incidence of 6-20 weeks). Spread via the fecal-oral route and inanimate objects contaminated with infected feces can spread the virus because of its ability to survive long periods of time in the environment. Symptoms occur 5-10 days after exposure. Older animals tend to fight off clinical disease, unless they are immune compromised. However, young animals can be drastically affected.

Canine rotavirus (CRV) can be an important cause of diarrhea, especially in puppies less than twelve weeks of age. It is not common in puppies older than twelve weeks. Rotavirus is spread through feces of infected puppies. The most common symptom is diarrhea. Almost all puppies will be under twelve weeks of age and most will be two weeks of age and less. Most cases of diarrhea are relatively mild. However, some cases are fatal.

Most authorities do not consider canine rotavirus to be of major concern. This is because it is not commonly encountered and fatalities in normal puppies are rare. It should, however, be a consideration when puppies are encountered with diarrhea especially if around two weeks of age.

Canine herpes virus is another disease causing virus that primarily causes problems in younger puppies. The disease is generally asymptomatic in dogs infected when older than 1-2 weeks of age at the time of exposure. Disease caused by CHV is generally fatal in neonatal pups who lack immunity derived from their dams. The virus is usually transmitted due to poor animal husbandry conditions or shedding. See Carmichael, L. Neonatal Viral Infections of Pups: Canine Herpesvirus and Minute Virus of Canines (Canine Parvovirus-1). In: Carmichael L. (Ed.), "Recent Advances in Canine Infectious Diseases." Ithaca: International Veterinary Information Service (www.ivis.org), 1999; document no. A0102.1199.

Pups rarely die if they are 2-3 weeks old at the time of exposure. The duration of illness in newborn pups is 1 to 3 days. Signs consist of anorexia, dyspnea, pain upon abdominal palpation, in coordination and, often, soft, yellow-green feces. There may be a serous, or hemorrhagic nasal discharge. Petechia are common on the mucous membranes. Rectal temperatures are not elevated. Thrombocytopenia has been reported in dying pups. CHV also may cause occasional in utero infections that result in the death of fetuses or pups shortly after birth. The virus also has been isolated rarely from dogs with vaginitis, conjunctivitis and respiratory illness. Asymtomatically infected dogs, or dams who suffered in utero infections, remain latently infected and virus may be excreted for about 1 week in nasal secretions or in genital secretions, and, thereafter, at unpredictable intervals over periods of several months, or years. See Carmichael, document no. A0102. 1199. Low maternal antibodies in the puppies are often the reason for a puppy contracting the virus.

Accordingly, the art field is in search of a vaccine regiment to protect pups from Canine Minute Virus, Canine Herpes Virus, and Canine Rotavirus after whelp and until the pups' immune system becomes more developed.

SUMMARY OF THE INVENTION

Accordingly, embodiments of the present invention relate to multivalent vaccines for Canine Rota Virus (CRV), Canine Herpesvirus (CHV), and/or Canine Parvo Virus (CPV), such as Minute Virus of Canines (MVC or CPV-1). Other embodiments of the invention generally relate to methods of vaccination of canines against CRV, CHV, and/or CPV.

In particularly preferred embodiments, pups are vaccinated after whelp with an embodiment of a vaccine of the present invention. Such vaccine protecting the pups for a period of time sufficient to allow the pups' immune system to begin development. In other embodiment, the vaccination of the pups provides protection to the pups from CRV, CHV, and/or CPV.

In a particularly preferred embodiment of a method of the present invention, pups are vaccinated against CRV, CHV, and/or CPV by maternal antibody transfer. Various embodiments transfer maternal antibodies in the colostrums of the bitch. Such transfer being sufficient to deliver high maternal antibody titers to the pups. Said antibody titers sufficient to protect the pups until the pups' immune system begins to develop.

DETAILED DESCRIPTION OF THE INVENTION

As used herein, the term "colostrums" shall mean and refer to the original and ultimate nutritional supplement, is a special fluid secreted by the mammary glands of all mammals near the time of birthing. Colostrums are rich in immune factors, growth factors, vitamins, minerals, amino acids, and other healthful components.

As used herein, the term "vaccine(s)" means and refers to a product, the administration of which is intended to elicit an immune response(s) that can prevent and/or lessen the severity of one or more infectious diseases. A vaccine may be a live attenuated preparation of bacteria, viruses or parasites, inactivated (killed) whole organisms, living irradiated cells, crude fractions or purified immunogens, including those derived from recombinant DNA in a host cell, conjugates formed by covalent linkage of components, synthetic antigens, polynucleotides (such as plasmid DNA vaccines), living vectored cells expressing specific heterologous immunogens, or cells pulsed with immunogen. It may also be a combination of vaccines listed above As used herein, the term "antigen" means and refers to a virus, a bacteria, parts of a virus or bacteria or a foreign protein that acts to stimulate the immune system in an animal. The immune system can be stimulated to cause the white blood cells to attack and destroy the antigen or to produce a protein molecule, which attaches to the antigen and either kills the antigen or makes it inactive. As used herein, the term "antibody" means and refers a protein-containing molecule that an animal's immune system makes that reacts with an antigen to make it inactive.

Embodiments of the present invention generally relate to multivalent vaccines for animals.

In a particularly preferred embodiment of a method of the present invention, pups are vaccinated against CRV, CHV, and/or CPV by maternal antibody transfer. Various embodiments transfer maternal antibodies in the colostrums of the bitch. Such transfer being sufficient to deliver high maternal antibody titers to the pups. Said antibody titers sufficient to protect the pups until the pups' immune system begins to develop.

In various embodiments, a multivalent vaccine of the present invention comprises at least three antigens, a first antigen, a second antigen and a third antigen. Said vaccine and/or antigens are able to be administered to a bitch prior to whelping.

In an embodiment, vaccination of the bitch is performed within four days of whelp. In another embodiment, vaccination is performed within two days of whelp. In yet a further embodiment, vaccination is performed prior to whelp.

The vaccinations administer a sufficient titer of vaccine to the at least one puppy, whereby an effective amount of maternal antibody to each antigen is transferred at nurse to the puppy to impart protection from the virus. In an embodiment, at least one of the first antigen, the second antigen, or third antigen is canine herpesvirus (CHV). In another embodiment, at least one of the first antigen, the second antigen, or third antigen is canine rotavirus (CRV). In another embodiment, at least one of the first antigen, the second antigen, or third antigen is Canine Parvovirus (CPV), selected from the group consisting of Minute virus of canine (MVC, CPV-1) and Canine Parvovirus (CPV-2). In a preferred embodiment, the first antigen is CHV, the second antigen is CRV, and third antigen is CPV, selected from the group consisting of MVC and CPV-2.

In various embodiments, the first antigen, the second antigen and the third antigen are selected from the group consisting of live, attenuated live, killed, and any combination of the aforementioned.

To ensure an adequate maternal antibody transfer from the bitch to the at least one puppy, the at least one puppy is allowed to nurse after whelp within at time selected from within twenty-four (24) hours and within forty-eight (48) hours.

After nursing, in an embodiment, the titer of CHV one week post whelp in the at least one puppy is greater than about 1:32. In another embodiment, the titer of CRV one week post whelp is greater than about 1:128. In another embodiment, the titer of MVC one-week post whelp is greater than about 1:32. In other embodiments, the titer of CHV two weeks post whelp is greater than about 1:32, the titer of CRV two weeks post whelp is greater than about 1:128, and the titer of MVC two weeks post whelp is greater than about 1:32.

Embodiments of the present invention further contemplate methods. Exemplary methods of the present invention include, but are not limited to, a method of vaccinating a puppy against at least one of canine herpesvirus (CHV), canine rotavirus (CRV), and Canine Parvovirus (CPV), selected from the group consisting of Minute virus of canine (MVC, CPV-1) and Canine Parvovirus (CPV-2) comprising the steps of administering a vaccine to the bitch prior to whelp comprising a CHV antigen, a CRV antigen, and/or a CPV antigen and allowing at least one of the puppies to nurse within about forty-eight (48) hours of whelp. Further embodiments allow at least one of the puppies to nurse within about 24 hours. In preferred embodiments, after nursing, the at least one puppy is vaccinated against CHV, CRV, and CPV.

Further embodiments of methods of the present invention include a method of vaccinating a puppy for protection against canine herpesvirus (CHV), canine rotavirus (CRV), and Canine Parvovirus (CPV), selected from the group consisting of Minute virus of canine (MVC, CPV-1) and Canine Parvovirus (CPV-2) comprises the steps of vaccinating a bitch with a vaccine comprising an antigen of CHV, an antigen of CRV, and an antigen of CPV prior to whelp and administering colostrums of the bitch to at least one puppy within about forty-eight (48) hours of whelp whereby maternal antibodies are transferred at a sufficiently high titer to protect the puppy from disease caused by CHV, CRV and CPV. Further embodiments comprise administering the colostrums to the puppy within about twenty-four (24) hours after whelp. However, various other methods of the present invention combine the teachings herein presented and the exemplary methods are not meant to be limiting.

While the invention has been described in connection with specific embodiments thereof, it will be understood that it is capable of further modifications and the appended claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended claims are intended to cover such differences. Furthermore, all patents, patent applications, articles, and other publications mentioned herein are herby incorporated by reference.

For a further understanding of various embodiments of the present invention, reference should be had to the following examples:

EXAMPLES

I. Purpose

The purpose of this study in pregnant dogs was to demonstrate maternal antibody transfer to pups from bitches vaccinated with an inactivated canine vaccine containing canine herpesvirus (CHV), canine rotavirus (CRV) and Minute virus of canine (MVC). Based on serology results, this preliminary study established that the experimental inactivated vaccine formulation is a feasible vaccine candidate for development.

II. Materials and Methods

A. Animals

Four breeding bitches shown to be seronegative against CHV, CRV and MVC were purchased from a commercial breeder. At the site of the commercial breeder the 4 bitches were assigned to one of two groups (Table 1). After being bred each bitch was housed in a separate isolation room. Pregnancy was determined at 3 weeks post-mating by ultrasound. To confirm seronegative status, a blood sample was obtained from each adult female prior to vaccination. The serum was tested for antibodies to MVC (CPV1), CRV and CHV using a constant virus-varying serum virus neutralization (VN) test. The two bitches assigned to Group I were vaccinated with the experimental inactivated canine vaccine containing canine herpesvirus (CHV), canine rotavirus (CRV) and Minute virus of canine (MVC). Bitches assigned to Group II remained as non-vaccinated controls. After whelping, bitches and pups were fed a standard, growth or maintenance dog chow and allowed water ad libitum. Veterinary care and treatment for non-study related health issues were provided for all animals throughout the study period.

B. Vaccination

Each of the pregnant bitches in Group I received two, 1-ml doses of the experimental, killed vaccine in the scruff of the neck via the subcutaneous (SC) route. The two vaccinations were administered three weeks apart. The first vaccination was given after pregnancy was determined, approximately three-weeks post-mating.

II. B. Vaccination

TABLE 1

STUDY PROTOCOL FOR EXPERIMENTAL VACCINATION (CHV/CRV/MVC) IN PREGNANT BITCHES

| Groups | No. of Bitches | Vaccine | Number of Vaccinations | Route |
|---|---|---|---|---|
| Vaccinate Group I | 2 | CHV/CRV/MVC | 2 | SC |
| Non-Vaccinates Group II | 2 | NA | 0 | NA |

C. Vaccine

The experimental vaccine was prepared in Intervet R&D facilities in Millsboro, Del. The vaccine was prepared using tissue culture derived virus inactivated with 20 mM BEA for 24 hrs. The MVC, CRV and CIV components used to create this vaccine were produced at maximum passage levels. Maximum production level for Master Seed MVC is X+3 on WRCC cells (X+17). Maximum production level for Master Seed CRV is X+5 on MARC 145 (X+4). Maximum production level for Master Seed CHV is x+5 on MDCK cells (X+14). The final vaccine was derived from non-concentrated bulk antigens and contained $\geq$10% CPV, $\geq$20% CRV and $\geq$55% CHV. In order to maximize maternal antibody response to CHV, MVC and CRV the experimental vaccine was formulated so as to contain 15% of Emulsigen® a product of MVP Laboratories Inc. Sterility and safety testing on the vaccine were conducted in Quality Control.

D. Serology

Antibody titers for bitches were determined at pre-vaccination, vaccination, and at 3 weeks post-first vaccination by methods common in the art. Blood samples were taken from bitches and pups at 1 and 2 weeks post-whelping as well. On each bleed date, a 5-ml volume of blood and 0.5 ml volume of blood was drawn from bitches and pups, respectively. Due to limited volume of serum from puppies some serum samples drawn on the same bleed date were pooled (Control pups). A standard serum-neutralizing test was conducted on all blood samples to indicate whether antibody responses were elicited and to identify the onset of responses.

III. Post-Vaccination Observations

All bitches were examined daily for 14 days post-first and second vaccination. No untoward reaction attributable to the vaccine was observed during the observation periods. In addition, no unfavorable reactions attributable to the vaccine were observed in the puppies during the 7-day post-whelping observation period. The lack of post-vaccination clinical observations in vaccinated bitches and their puppies indicate that the experimental vaccine is safe.

IV. Results

This experiment demonstrated maternal antibody transfer to pups from bitches vaccinated with an experimental trivalent vaccine containing CHV, CRV, and MVC. As is illustrated in Tables 2 and 3, the vaccinated bitches, bitch #1 and bitch #2, responded serologically to each of the two vaccinations. Furthermore this study demonstrates that the transfer of maternal antibodies to puppies was at levels protective against CRV, CHV and MVC. Conversely the two non-vaccinated bitches, bitch #3 and bitch #4, and their puppies remained antibody negative for CRV, MVC and CIV during the study period (Table 4). Due to non-specific CRV neutralization associated with serum from non-vaccinated dogs, CRV titers $\leq$1:128 were considered negative. These results illustrate that the level of maternal antibody transferred from bitches vaccinated with a multivalent vaccine of the present invention to their pups after nursing is sufficient to establish the feasibility of this vaccine.

The results of this preliminary vaccination study in pregnant dogs have demonstrated maternal antibody transfer to pups from bitches vaccinated with experimental inactivated canine vaccine containing canine rotavirus, canine herpesvirus and minute virus of canine. Based on serology results, this study establishes that a multivalent vaccine may be administered to a bitch prior to whelp whereby maternal antibodies, of sufficient titer, are transferred to the pups through the colostrums.

| Sample | | | CRV (VN) | CHV (VN) | MVC (VN) |
|---|---|---|---|---|---|
| Vaccinates bitches and puppies | | | | | |
| Bitch # 1 | | | | | |
| | | pre-1$^{st}$ vac | 1:128 | 1:2(VN) | <2 |
| | | pre-2$^{nd}$ vac | >1:1024 | 1:256 | 1:128 |
| | | 1 week post-whelp | >1:1024 | 1:64 | 1:256 |
| Pup # | 2 | 1 week post-whelp | 1:64 | 1:32 | 1:64 |
| | 3 | 1 week post-whelp | 1:1536 | 1:64 | 1:256 |
| | 5 | 1 week post-whelp | 1:768 | 1:64 | 1:32 |
| | 6 | 1 week post-whelp | 1:192 | 1:16 | 1:128 |
| | | 2 weeks post-whelp | 1:1024 | 1:64 | 1:128 |
| Pup # | 2 | 2 weeks post-whelp | 1:64 | 1:16 | 1:4 |
| | 3 | 2 weeks post-whelp | 1:512 | 1:32 | 1:128 |
| | 5 | 2 weeks post-whelp | 1:512 | 1:64 | 1:32 |
| | 6 | 2 weeks post-whelp | 1:256 | 1:16 | 1:8 |
| Bitch # 2 | | | | | |
| | | Pre-1$^{st}$ vac | 1:62 | 1:≦2 | 1:≦2 |
| | | Pre-2$^{nd}$ vac | 1:256 | 1:8 | 1:32 |
| | | 1 wk post whelp | 1:8192 | 1:32 | 1:64 |
| Pup # | 1 | 1 wk post whelp | 1:224 | 1:8 | 1:8 |
| | 2 | 1 wk post whelp | 1:384 | 1:16 | 1:16 |
| | | 2 wk post whelp | 1:8192 | 1:32 | 1:16 |
| Pup # | 1 | 2 wk post whelp | 1:160 | 1:8 | 1:16 |
| | 2 | 2 wk post whelp | 1:320 | 1:8 | 1:4 |
| Non-vaccurates (Controls) | | | | | |
| Bitch # 3 | | | | | |
| | | 1-wk post whelp | 1:128 | 1:≦2 | 1:≦2 |
| Pup # | 1 | 1-wk post whelp | 1:96 | 1:≦2 | 1:8 |
| | 2 | 1-wk post whelp | 1:144 | 1:≦2 | 1:≦2 |
| | 3 | 1-wk post whelp | ND | 1:≦2 | 1:≦2 |
| | 4 | 1-wk post whelp | ND | 1:≦2 | 1:4 |
| | | 2-wk post whelp | 1:64 | 1:≦2 | 1:≦2 |
| Pup # | 1 | 2-wk post whelp | 1:80 | 1:≦2 | 1:≦2 |
| | 2 | 2-wk post whelp | 1:96 | 1:≦2 | 1:4 |

-continued

| Sample | | | CRV (VN) | CHV (VN) | MVC (VN) |
|---|---|---|---|---|---|
| Bitch # 4 | | | | | |
| | | 1-wk post whelp | 1:128 | 1:≦2 | 1:≦2 |
| Pup # | Pool 2 + 3 | 1-wk post whelp | 1:48 | 1:≦2 | 1:≦2 |
| | | 2-wk post whelp | 1:128 | 1:≦2 | 1:≦2 |
| Pup # | Pool 2 + 3 | 2-wk post whelp | 1:64 | 1:≦2 | 1:≦2 |

What we claim is:

1. A vaccine comprising an immunogenically effective amount of an inactivated whole Minute virus of canine (MVC, also known as Canine Parvovirus-1 (CPV-1)).

2. The vaccine of claim 1 further comprising at least one additional antigen selected from the group consisting of a canine herpesvirus (CHV) antigen, a canine rotavirus (CRV) antigen, and a Canine Parvovirus type 2 (CPV-2) antigen.

3. The vaccine of claim 2 wherein the at least one additional antigen is an inactivated virus.

4. The vaccine of claim 2 wherein the at least one additional antigen is an attenuated live virus.

5. A method of protecting a puppy against Minute virus of canine (MVC, also known as Canine Parvovirus-1 (CPV-1)) comprising
   i) administering a vaccine comprising an immunogenically effective amount of an inactivated whole MVC to a pregnant bitch prior to whelp, and
   ii) administering colostrums of the bitch to at least one puppy within about forty-eight (48) hours of whelp whereby maternal antibodies are transferred at a sufficiently high titer to protect the puppy from disease caused by MVC.

6. The method of claim 5, comprising administering colostrums of the bitch to at least one puppy within about 24 hours of whelp.

7. The method of claim 5, wherein the maternal antibodies are transferred by allowing the puppy to nurse the bitch within about forty-eight (48) hours of whelp.

8. The method of claim 7, wherein the maternal antibodies are transferred by allowing the puppy to nurse the bitch within about 24 hours of whelp.

9. The method of claim 5, wherein the vaccine further comprises at least one additional antigen selected from the group consisting of a canine herpesvirus (CHV) antigen, a canine rotavirus (CRV) antigen, and a Canine Parvovirus type 2 (CPV-2) antigen.

10. The method of claim 9, wherein the at least one additional antigen is an inactivated virus.

11. The method of claim 9, wherein the at least one additional antigen is an attenuated live virus.

* * * * *